(12) United States Patent
Gindilis

(10) Patent No.: US 8,234,905 B2
(45) Date of Patent: Aug. 7, 2012

(54) SELECTIVELY FUNCTIONIZED TRANSDUCER MICROARRAY

(75) Inventor: Andrei L. Gindilis, Vancouver, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 1009 days.

(21) Appl. No.: 12/185,253

(22) Filed: Aug. 4, 2008

(65) Prior Publication Data
US 2012/0164351 A1   Jun. 28, 2012

(51) Int. Cl.
*G01N 33/53* (2006.01)
*G01N 37/00* (2006.01)

(52) U.S. Cl. .......................................................... 73/1.01
(58) Field of Classification Search .................... 73/1.01
See application file for complete search history.

(56) References Cited

U.S. PATENT DOCUMENTS

| | | | | |
|---|---|---|---|---|
| 5,667,667 | A | * | 9/1997 | Southern ........................ 205/687 |
| 6,093,302 | A | * | 7/2000 | Montgomery ................. 205/122 |
| 6,458,600 | B1 | | 10/2002 | Mirsky et al. |
| 2006/0102471 | A1 | * | 5/2006 | Maurer et al. ............ 204/290.01 |

FOREIGN PATENT DOCUMENTS

| | | |
|---|---|---|
| JP | 2003510584 | 3/2003 |
| JP | 2006-28469 | 9/2006 |
| WO | WO9927355 | 6/1999 |
| WO | WO 01/23082 | 4/2001 |

OTHER PUBLICATIONS

Dill K. et al "Multiplexed Analyte and Oligonucleotide Detection on Microarrays Using Several Redox Enzymes in Conjunction with Electrochemical Detection", Lab Chip, vol. 6, 2000, pp. 1052-1055.*
Nakajima, N. et al., "Mechanism of Amide Formation by Carbodiimide Bioconjugation in Aqueous Media", Bioconjugate Chemistry, vol. 6, 1995, pp. 123-130.
Zhu et al., Catch and release cell sorting: Electrocmehical desorbtion of T-cells from antibody-modified microelectrodes. Colloids and Surfaces B; Biointerface, vol. 64, 2008, pp. 260-268.
Chen et al., "Interfacial design and fucntionalization on metal electrodes through self-assembled monolayers", Surface Science Reports, vol. 61, No. 11, Dec. 1, 2006, pp. 445-463.
Wilson et al., "Biosensors for real-time in vivo measurement", Biosensors and Bioelectronics, vol. 20, No. 12, Jun. 15, 2005, pp. 2388-2403.

* cited by examiner

*Primary Examiner* — Daniel Larkin
(74) *Attorney, Agent, or Firm* — Law Office of Gerald Maliszewski; Gerald Maliszewski

(57) ABSTRACT

A system and method are provided for selectively functionalizing a transducer microarray. The method provides a microarray including a field of transducers exposed to a shared local environment. A difference in the pH associated with the transducers is created. As a result, functional molecules are selectively bound to transducers in response to the pH associated with the transducers. In one aspect, the microarray also provides a field of transducer pH-generating electrodes, one pH-generating electrode for each transducer, and a counter electrode. The difference in pH associated with the transducers is created by selectively applying a voltage potential between pH-generating electrodes and the counter electrode, to create a difference of pH in regions adjacent to the transducers.

7 Claims, 15 Drawing Sheets

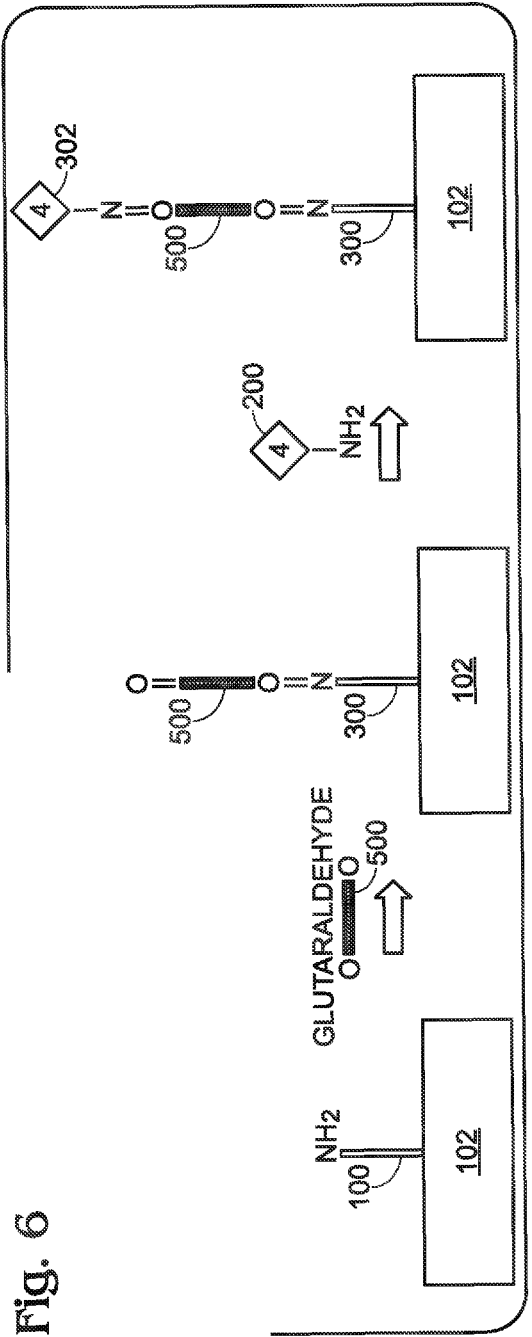
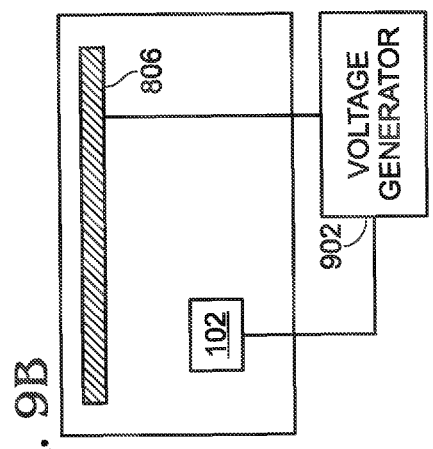
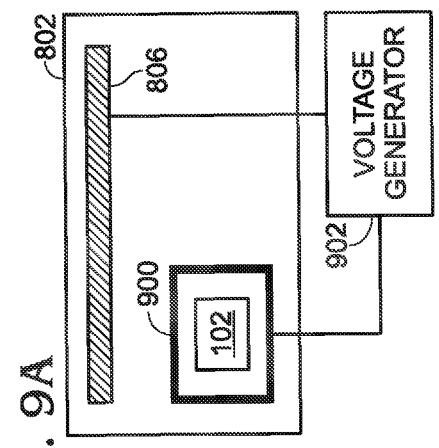

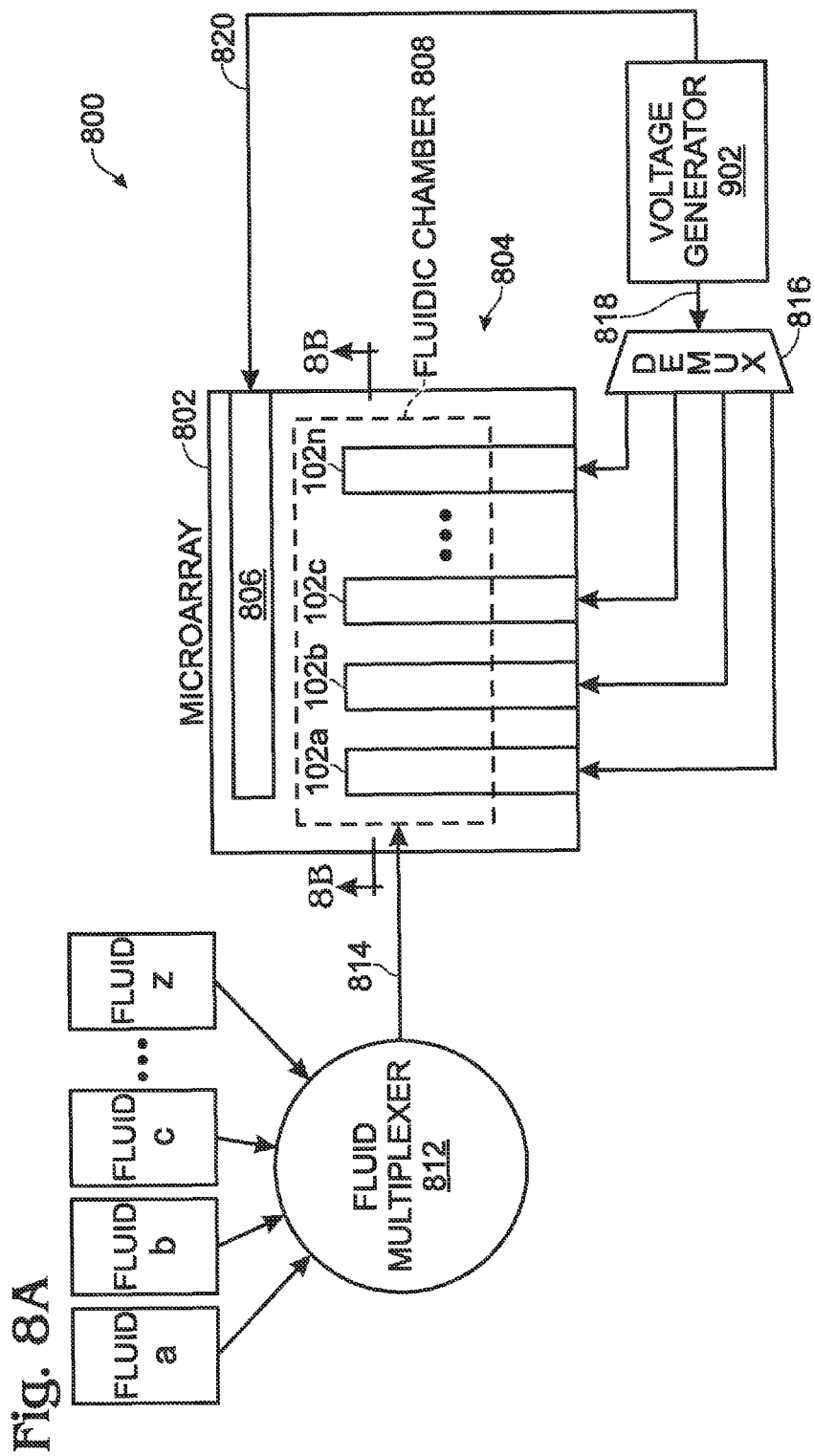

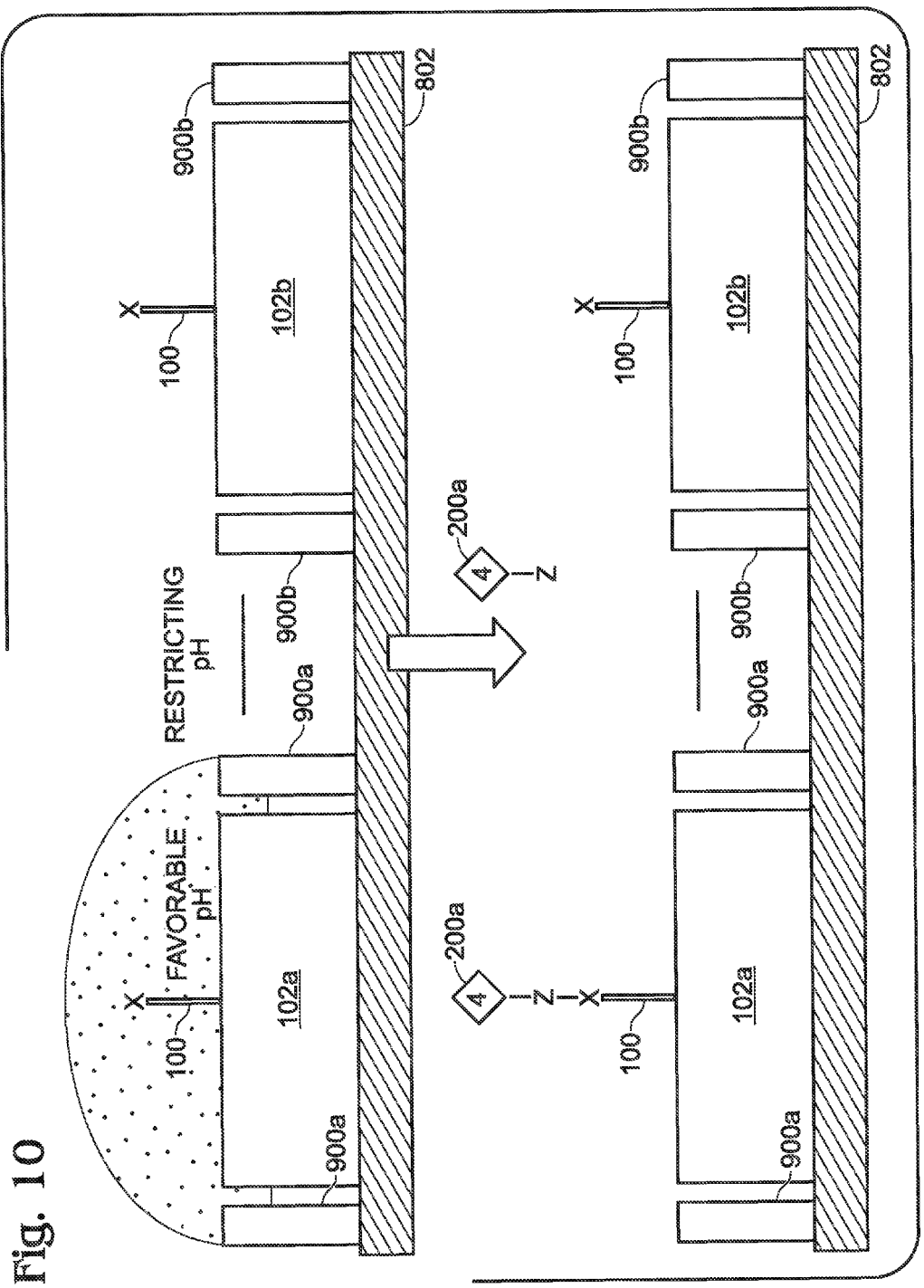

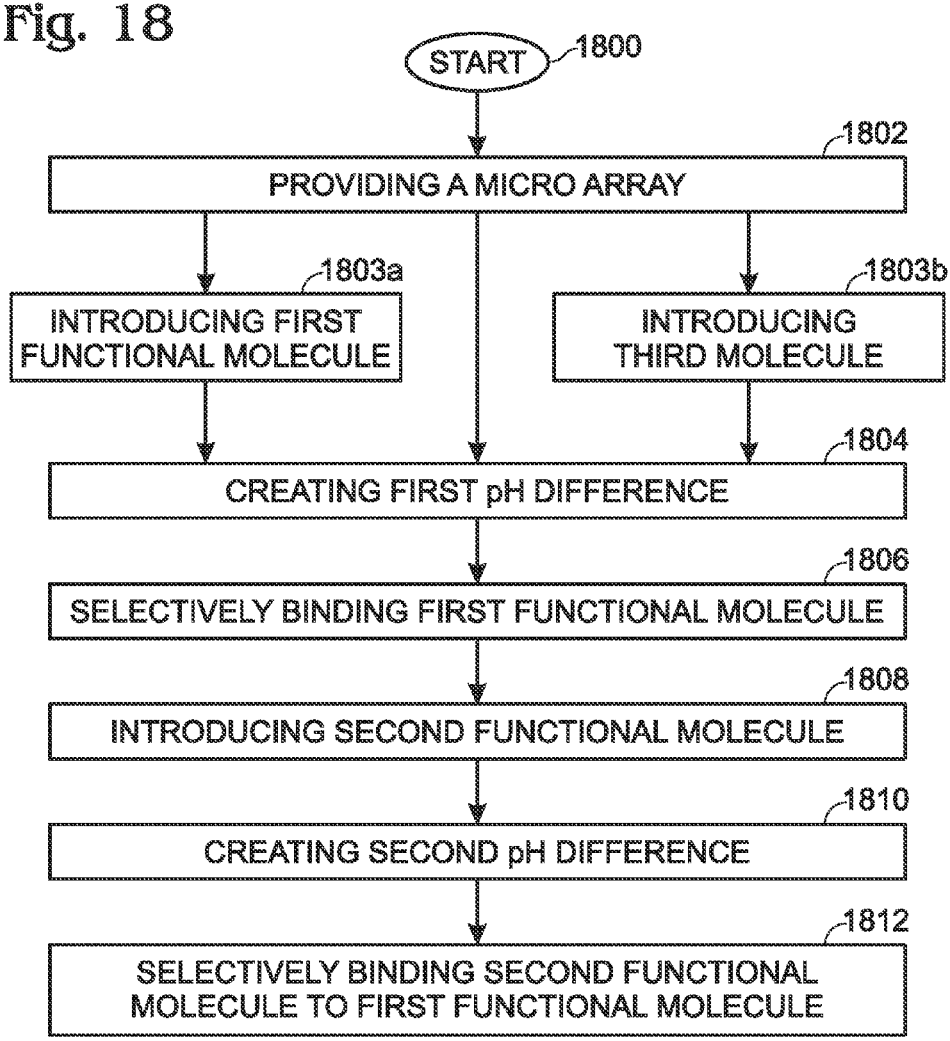

SELECTIVELY FUNCTIONIZED TRANSDUCER MICROARRAY

BACKGROUND OF THE INVENTION

1. Field of the Invention

This invention generally relates to biological analyte measurement and, more particularly, to a method for functionalizing a multiple-analyte transducer microarray.

2. Description of the Related Art

Microarray technology is a power research tool that permits the assaying of multiple analytes in a single sample—a multiplexed assay format. To perform such assay, a microarray has to contain multiple transducers modified with different bio-components. Selective attachment of a desired bio-component to a particular transducer constitutes one of the biggest challenges in the microarray technology. At present, the major approaches for microarray multiplexing are: (i) spotting of different bio-components over an array; (ii) physical separation of transducers via a nano-fluidic set of connections, and target delivery of bio-components to pre-selected transducers; (iii) self-assembling of tagged bio-components on an array surface that is modified with an agent capable of the specific capturing of bio-component tags; and (iv) controlled synthesis of bio-components on the surface of transducers. All these approaches have limitations in terms of costs and ease of mass manufacturing.

The spotting technology approach (i) is based on the target delivery of certain bio-components to selected transducers (spots) on the array, followed by attachment to the array surface. The spotting approach has serious limitations regarding the size and shape of the transducers that can be used. The approach of controlled delivery of bio-components (ii) to selected transducers on the array via micro, or a nano-fluidic set of connections, requires expensive instrumentation. The self assembling technology (iii) converts an oligonucleotide array into an immuno-array by using bio-components (antibodies) modified with specific oligonucleotide tags (K. Dill, K. Schwarzkopf, and A. Ghindilis, Multiplexed Analyte and Oligonucleotide Detection on Microarrays Using Several Redox Enzymes in Conjunction With Electrochemical Detection, *Lab on a Chip*, (2006) 6, 1052-1055). The specific hybridization of bio-component tags with array oligonucleotide probes results in immobilization on the surface of array transducers. The advantage of the approach is the simplicity of a one-stage procedure of array conversion. However, the technology requires very expensive semiconductor-based in situ synthesized oligonucleotide arrays. The approach of controlled synthesis of bio-components (iv) on the array surface is based on photolithography (Affymetrix®), ink-jet printing (Agilent Technologies), or electrochemistry (CombiMatrix). In all cases, a multi-stage process is used in the control of phosphoamidite chemistry by manipulation with a blocking agent on each array transducer. At present, this approach is only applicable for in situ synthesis of oligonucleotide arrays, and the synthesis itself is quite expensive.

It would be advantageous if there was a simpler and more cost-effective way for the attachment of bio-components onto selected transducers of a multi-analyte microarray.

SUMMARY OF THE INVENTION

Described herein is a method and instrumentation for the attachment of bio-components onto selected transducers of a microarray via pH controlled immobilization. The approach employs either the positioning of an individually addressable electrode in close proximity to each transducer, or alternatively, the creation of a transducer design that directly enables a transducer surface with an electrical input. The pH control is based on electrochemical generation of either protons or hydroxyls in the vicinity of a transducer. Sequential immobilization of various bio-components under pH-controlled conditions permits fabrication of an array in a desired configuration.

Accordingly, a method is provided for selectively functionalizing a transducer microarray. The method provides a microarray including a field of transducers exposed to a shared local environment. A difference in the pH associated with the transducers is created. As a result, functional molecules are selectively bound to transducers in response to the pH associated with the transducers. In one aspect, the microarray provides a field of transducer pH-generating electrodes, one pH-generating electrode for each transducer, and a counter electrode. The difference in pH associated with the transducers is created by selectively applying a voltage potential between pH-generating electrodes and the counter electrode, to create a difference of pH in regions adjacent to the transducers.

For example, the method may introduce first functional molecules to the environment. Then, the pH associated with a first transducer is modified, while maintaining the pH associated with a second transducer. As a result, the first functional molecules from the environment are bound to the first transducer, but not the second transducer. In another aspect, selectively binding the functional molecules to transducers includes disassociating a bond between functional molecules and transducer surfaces, responsive to the pH associated with the transducers.

Additional details of the above described method and a system for selectively functionalizing a transducer microarray are provided below.

BRIEF DESCRIPTION OF THE DRAWINGS

FIG. 6 depicts an example of the multi-stage process depicted in FIG. 5, where the initially bound functional group and subsequently added biological component are modified.

FIGS. 8A and 8B are schematic block diagrams depicting a system for selectively functionalizing a transducer microarray.

FIGS. 9A and 9B are schematic block diagrams depicting an exemplary transducer, pH-generating electrode, and counter electrode from of the microarray of FIG. 8.

FIG. 10 presents an example of the pH-controlled immobilization of a bio-component initially bound with, or functionalized with a group Z.

FIG. 18 is a flowchart illustrating a method for selectively functionalizing a transducer microarray.

DETAILED DESCRIPTION

Transducer and Sensing Element

Figure 1A:
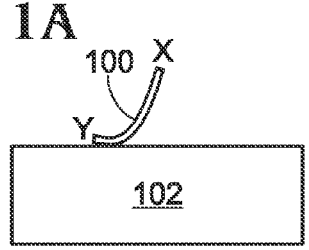
FIGS. 1A through 1D are schematic diagrams depicting the attachment of a functionalized molecule to the surface of a transducer.

A transducer is a detector capable of generating a physical signal (output) in response to alterations of biological or chemical environment in the vicinity of the transducer's surface. The signal may be visual or electrical, for example. These alterations occur when a pre-selected biological component that is attached to the transducer's surface specifically interacts with a target analyte, which is the process of bio-recognition. The transducer integrated with the biological component forms a sensing element of a biosensor.

Biological Components of the Sensing Element: Bio-Recognition Components

The biological component responsible for bio-recognition is a molecule capable of specific binding with the target analyte, specific transformation of the corresponding target analyte, or both. An analyte is a substance or chemical constituent that is determined in an analytical procedure, such as a titration. For instance, in an immunoassay, the analyte may be the ligand or the binder, while in blood glucose testing, the analyte is glucose. In medicine, the term "analyte" often refers to the type of test being run on a patient, as the test is usually determining a chemical substance in the human body. An analyte cannot typically be measured, but a measurable property of the analyte can be. For instance, glucose cannot be measured, but glucose concentration can be measured. In this example "glucose" is the component and "concentration" is the property. In laboratory and layman jargon the "property" is often left out provided the omission does not lead to an ambiguity of what property is measured.

Biological components include oligonucleotides, DNA/RNA molecules or their fragments, peptides, receptors, antibodies, enzymes, whole cells and cellular fragments, etc. In some applications biotin and streptavidin can also be considered as biological components.

Transducer Surface

The transducer surface can be conductive, semi-conductive, or non-conductive. The surface material can be metal or alloy, such as gold, platinum, aluminum, chrome, or silica, carbon-based, such as graphite or glassy carbon, glass, ceramic, a composite, such as silicon nitride or indium tin oxide (ITO), or a plastic such as polystyrene or nylon.

Transducer Surface Modification

The initial modification of the transducer surface introduces functional groups that are capable of binding other biological components to the sensing element. The introduction of the functional groups to the transducer surface can be performed in one of the following ways:

Direct chemical conversion of the transducer surface. For example, a carbon-based surface can be oxidized using oxygen plasma or an oxidant such as nitric acid.

Surface modification by coating with polymer that contains functional groups in its structure. The polymer coating results in introduction of the groups onto the transducer surface. The polymer can be a biopolymer (poly-sugar, gelatin, etc), polyethyleneimine, polyacrylic acid, hydro-gel (polyvinyl alcohol, silica gel, etc.), nylon, etc.

Functionalization

Functionalization describes the modification of a transducer surface with attached bio-probe molecules capable of specific biological recognition of analyte molecules. Biological recognition is an ability of the bio-probe molecule to specifically bind or catalytically convert analyte molecules.

Functional Groups

Functional groups are specific groups of atoms within molecules that are responsible for the characteristic chemical reactions of those molecules. The same functional group undergoes the same or similar chemical reaction(s) regardless of the size of the molecule of which it is part. However, its relative reactivity can be modified by nearby functional groups.

Activation

Activation a process of enabling functional groups to interact with each other by creating corresponding chemical and physical conditions. For example, carboxyl and amino groups are capable of binding to each other. However, the binding event requires both (i) a presence of carbodiimide and (ii) a certain pH value of the medium. Therefore, in the absence of either one of these conditions the carboxyl group is not active to bind amino group. Only the presence of carbodiimide and a certain pH value of the medium make the carboxyl group active. Some functional groups do not require an additional chemical component to bind a second functional group. For example, aldehyde groups are active for binding amino groups without any additional chemical added. However, the pH of the media almost always has to be adjusted to some certain value to make a functional group active for binding.

Functional Molecule

A functional molecule is a molecule that contains functional groups capable to bind another molecule that contains corresponding functional groups.

FIGS. 1A through 1D are schematic diagrams depicting the attachment of a functionalized molecule to the surface of a transducer. The functionalized molecule 100 consists of two functional groups, X and Y, separated by a spacer. The functional groups X and Y can be an amino, a carboxyl, an aldehyde, an oxy, a thiol, a biotin, an oligonucleotide, a peptide, or a streptavidin, for example. The X and Y groups may also be of the same structure as the spacer. The spacer can be a hydrocarbon, a carbohydrate, an oligonucleotide, a peptide, a linear polymer, or a streptavidin/avidin, for example. The X and Y groups can also be connected to each other without a spacer (not shown).

As shown in FIG. 1A, interaction of the functionalized molecule 100 with the transducer 102 surface can be achieved by absorption or hydrophilic/hydrophobic interaction of the Y group onto the transducer surface. For example, when the transducer 102 surface is graphite, the Y group may be hydrophobic —$(CH_2)nCH_3$ tail.

Figure 1C:
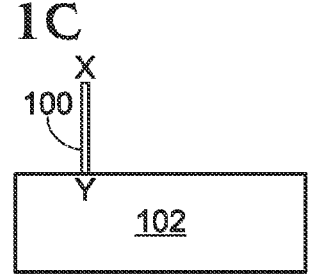
Figure 1B:
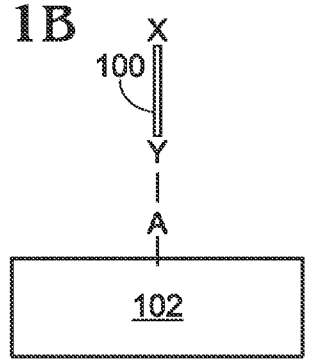

In FIG. 1B, a chemical interaction of the Y group with A groups on the transducer 102 surface result in an A—Y bond or an A—Y complex formation. For example, when the transducer 102 surface is oxidized graphite, the Y group may be an amino group that binds to carbodiimide-activated COO. group of the surface.

In FIG. 1C, the Y group is incorporated onto the surface of the transducer. For example, if the transducer 102 surface is gold, the Y group may be an SH group that binds to the gold surface, due to the sulfur to gold affinity.

Figure 1D:
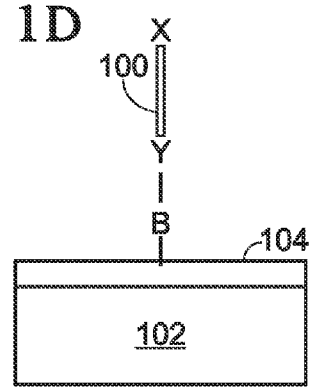

In FIG. 1D, the chemical interaction of the Y group with B groups of a polymer coating layer 104 on the transducer 102 surface results in a B—Y bond or a B—Y complex formation. For example, if the transducer 102 surface is coated with polyethyleneimine, the Y group may be an aldehyde that binds to an $NH_2$ group of the polymer, forming a Schiff base. In all the above-mentioned cases, the functionalized molecule 100 binds to the transducer 102 surface with the Y terminal end. The functional group X is exposed to the external side of the surface (the environment).

Immobilization of Biological Components on the Transducer Surface.

Figure 2:
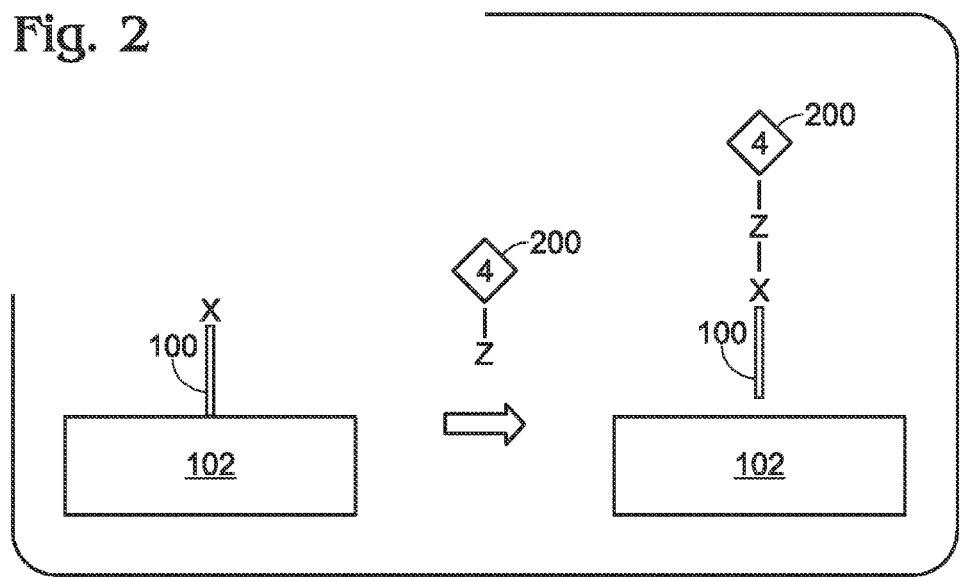
FIG. 2 is a schematic diagram depicting an interaction of the functionalized transducer of FIG. 1A, 1B, 1C, or 1D, with a biological component.

FIG. 2 is a schematic diagram depicting an interaction of the functionalized transducer of FIG. 1A, 1B, 1C, or 1D, with a biological component 200. After the transducer 102 surface is pre-modified with the functional group X, it can now interact with the Z group of the biological component 200 forming a X—Z bond or a X—Z complex. The Z group can be (i) natively present as a part of the biological component molecule (amino and carboxyl groups of proteins); (ii) introduced into the biological component molecule via chemical/biological modification (an oligonucleotide tag coupled to a protein molecule); or, (iii) introduced into the molecule at some stage of chemical synthesis of the biological component (an amino group of a synthetic oligonucleotide). The Z group can be an amino, a carboxyl, an aldehyde, an oxy, a thiol, a biotin, an oligonucleotide, a peptide, or a streptavidin, for example.

Figure 3A:
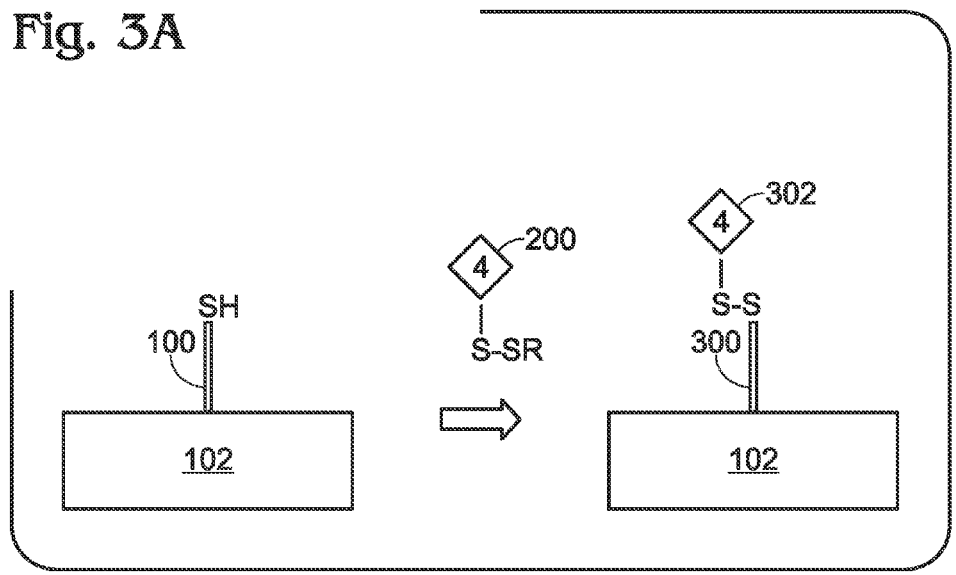
FIGS. 3A and 3B are examples of a modified biological component being bound to a modified functional molecule.
Figure 3B:
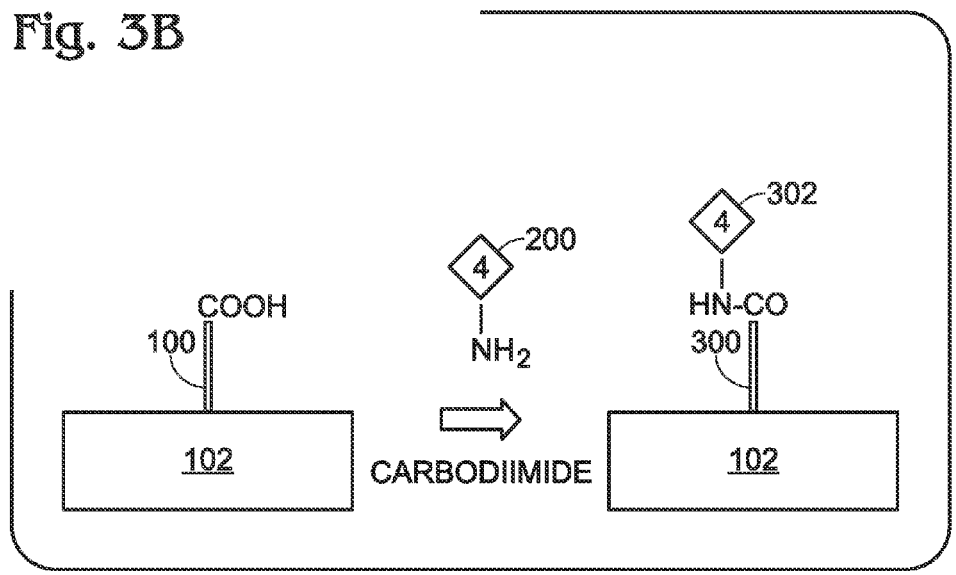

FIGS. 3A and 3B are examples of a modified biological component being bound to a modified functional molecule. In FIG. 3A, the transducer 102 surface is bound to an SH group functional molecule 100. This group binds to the disulfide group of a pre-modified bio-component 200, such as oligo-nucleotide, forming the S—S bond. That is, the functional molecule 100 is modified to form modified functional molecule 300, and the biological component 200 becomes modified biological component 302.

In FIG. 3B, the carbodiimide-activated carboxyl-modified modified functional molecule 300 binds to a modified bio-component molecule 302, such as protein, that contains amino groups.

Figure 4:
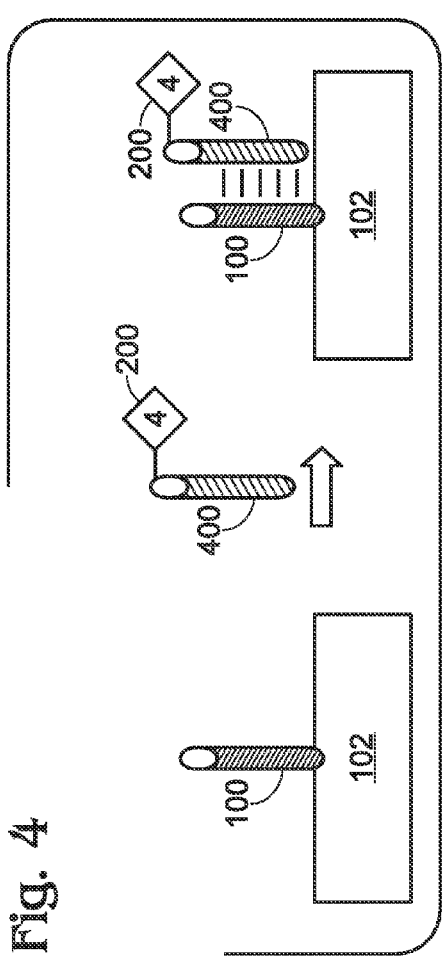
FIG. 4 is a schematic diagram depicting the binding of a hybridized functional molecule with a biological component.

FIG. 4 is a schematic diagram depicting the binding of a hybridized functional molecule with a biological component. The transducer 102 surface is bound to an oligonucleotide functional molecule. The biological component 200 molecule includes a corresponding complementary oligonucleotide tag 400. Hybridization of the functional molecule oligonucleotide 100 with the tag 400 of the biological component 400 leads to attachment of the latter to the transducer 102 surface.

Figure 5:
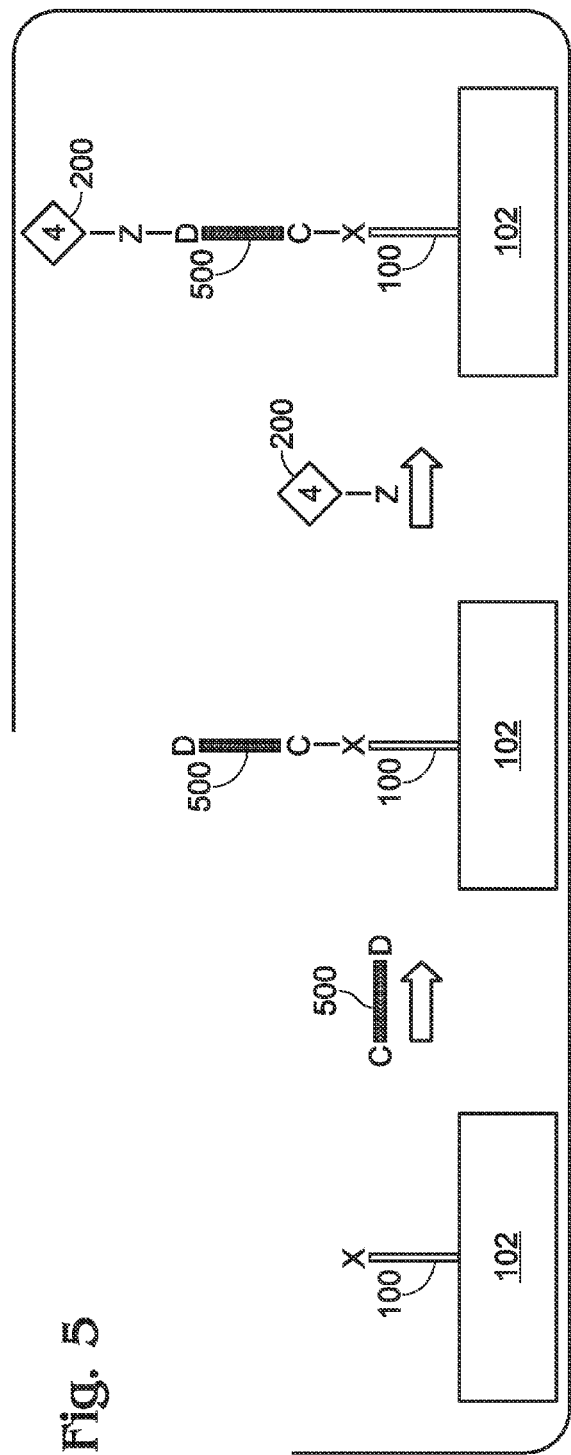
FIG. 5 is a schematic diagram depicting a multi-stage functionalization of a transducer surface.

FIG. 5 is a schematic diagram depicting a multi-stage functionalization of a transducer surface. In practice it is not always possible to introduce functional groups capable of high efficiency interactions onto the transducer surface and into a bio-component molecule. Thus, an additional stage of surface modification may be needed. FIG. 5 illustrates an immobilization procedure of a biological component that involves an additional stage. First, a molecule 500 that contains C and D functional groups separated with a spacer interacts with the functional molecule 100 bound to the transducer 102 surface. The group C binds to the group X, and the functional group D is exposed on the external side of the transducer surface (the environment). The subsequent steps are performed in a manner similar to the ones described in FIG. 2. The chemical nature of groups C, D, and the spacer is similar to that described above for the functional molecule 100 containing X and Y groups.

FIG. 6 depicts an example of the multi-stage process depicted in FIG. 5, where the initially bound functional group and subsequently added biological component are modified. The transducer 102 surface is attached to an amino group functional molecule 100. The amino group reacts with one of the aldehyde groups of a glutaraldehyde molecule 500 leading to an aldehyde group 300 attachment to the transducer 102 surface. Next, amino groups of the biological component 200 react with the aldehyde groups of the transducer surface, forming Schiff base bonds. That is, the biological component 200 becomes a modified biological component 302.

Figure 7:
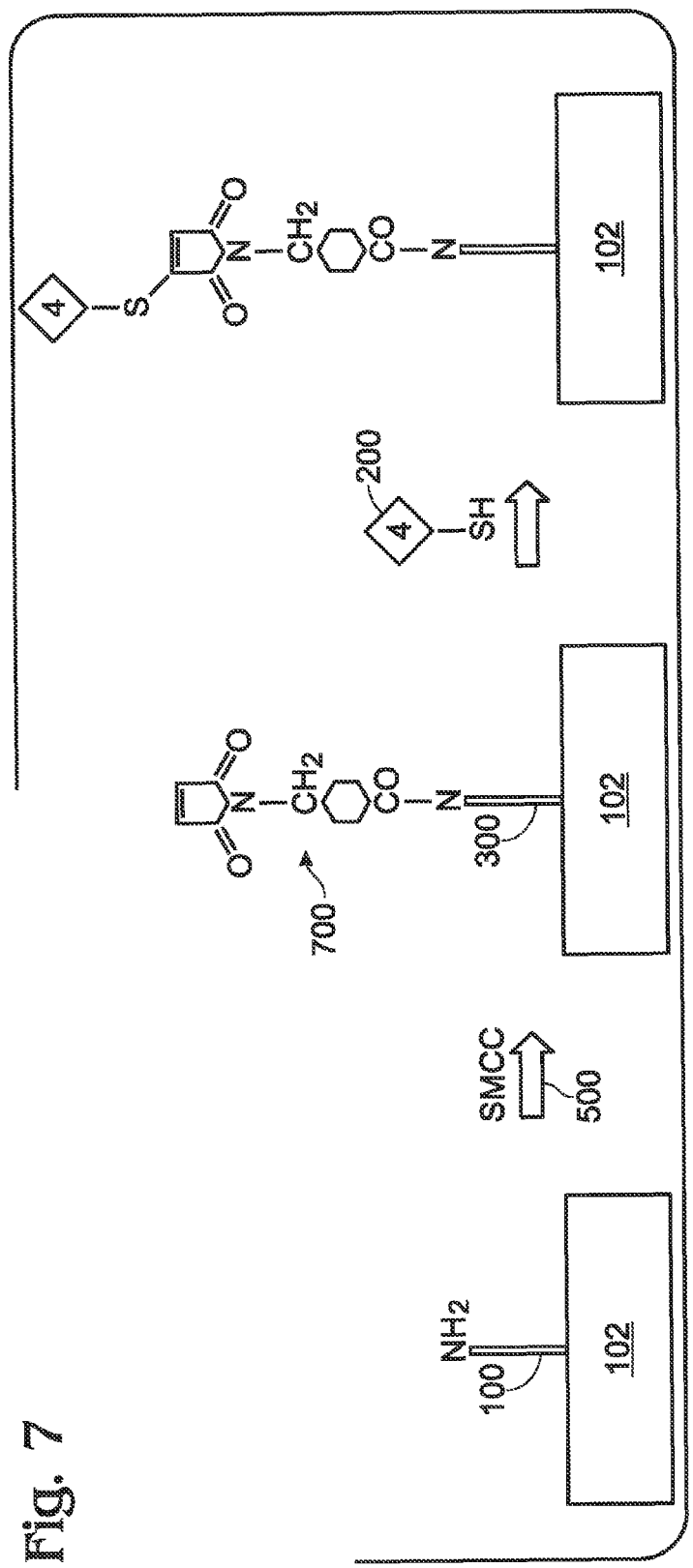
FIG. 7 depicts another example of a multi-stage process.

FIG. 7 depicts another example of a multi-stage process. The transducer 102 surface is attached to an amino group 100, and a bio-component molecule 200 contains a thiol group (SH). A molecule of SMCC 500 that contains both maleimide and succinimide functional groups is then introduced to the transducer 102 surface. This results in reaction of the amino group 100 of the transducer surface with the succinimide functional group, leading to a surface modification with a functional molecule 700 having the maleimide group capable of further interactions with the thiol group of the biological component 200.

Dependence of Immobilization on pH

The interactions of functional groups that result in the creation of either chemical bonds or complex formations depend upon the pH of the reaction medium. For example, 1-ethyl-3-(3-dimethylaminopropyl)carbodiimide hydrochloride (EDC) can react with carboxyl groups at a relatively narrow low pH range such as 3.5-4.5 (Nakajima N, Ikada Y, *Bioconjug Chem*., Mechanism of amide formation by carbodiimide for bioconjugation in aqueous media, 1995 January-February; 6(1):123-30). At high pH values, activation of carboxyl groups by EDC does not occur. Therefore, interaction between carboxyl groups and amino groups has to be performed at a certain pH range in the reaction medium to achieve N—C bond formation. For example, the immobilization process described in FIG. 3B takes place only within a narrow pH window. Immobilization of bio-components based on oligonucleotide tag hybridization (FIG. 4) is also very sensitive to pH of the reaction medium. At pH values even slightly higher then neutral, the oligonucleotide hybridization does not occur. Moreover, immobilization of bio-components based on oligonucleotide tag hybridization is a reversible process. A high pH value results in denaturing of hydrogen bonds of the oligonucleotide double helix and causes dissociation of the immobilized complex. Thus, pH of the reaction medium can be either favorable or restricting, and immobilization of bio-components on the transducer surface can be controlled by manipulating pH in the vicinity of the transducer surface.

FIGS. 8A and 8B are schematic block diagrams depicting a system for selectively functionalizing a transducer microarray. Starting with FIG. 8A, the system 800 comprises a microarray including a field of transducers 804 with an associated pH-generating electrode adjacent each transducer, and a counter electrode 806. Transducers 102a through 102n are shown, where n is not limited to any particular value.

FIGS. 9A and 9B are schematic block diagrams depicting an exemplary transducer, a pH-generating electrode, and a counter electrode from the microarray of FIG. 8. In FIG. 9A, the transducer 102 is surrounded, or adjacent to a pH-generating electrode 900. A voltage generator 902 creates a voltage potential between the pH-generating electrode 900 and the counter electrode 806. In FIG. 9B, the transducer 102 acts as the pH-generating electrode.

Returning to FIG. 8A, the system 800 further comprises a fluidic chamber 808 (shown in phantom) including a cavity (810, see FIG. 8B) to provide a shared local environment for the field of transducers 804. The fluidic chamber 808 can also be seen in the partial cross-sectional view of FIG. 8B.

Returning to FIG. 8A, a fluid multiplexer 812 is used to selectively supply fluids to the fluidic chamber 808 on line 814. Various fluids, fluids a through z, are supplied to the fluid multiplexer. A voltage demultiplexer 816 (DEMUX) is connected to the microarray to create a voltage between the counter electrode 806 and the pH-generating electrodes of selected transducers. The voltage is supplied to the DEMUX 816 on line 818 from voltage generator 902. The voltage generator 902 is also connected to the counter electrode 806 on line 820. In addition to supplying a demultiplexed voltage, the voltage generator can vary the potential difference and polarities of the voltages on lines 818 and 820. The demultiplexed voltage creates a difference in the pH associated with transducers, responsive to the pH in regions adjacent to the transducers, for selectively binding functional molecules to transducers.

Some examples of functional molecules that may be bound to transducers or introduced into the fluidic chamber include oligonucleotides, DNA, RNA, DNA fragments, RNA fragments, peptides, receptors, antibodies, enzymes, whole cells, cellular fragments, biotin, and streptavidin.

In one aspect, the fluid multiplexer 812 introduces a first functional molecule (e.g., fluid a) to the fluidic chamber 808. The voltage demultiplexer 816 modifies the pH associated with transducer 102a, while maintaining the pH associated with a transducer 102b, thereby binding the first functional molecules in the fluidic chamber 808 to the transducer 102a, but not to transducer 102b, see FIGS. 1A-1D.

Alternately, the voltage demultiplexer 816 may modify the pH associated with transducer 102a, while maintaining the pH associated with transducer 102b, as above. However in this aspect, the first functional molecules in the fluidic chamber 808 bind to transducer 102b, but not to transducer 102a. In another aspect, the voltage demultiplexer 816 disassociates a bond between functional molecules bound to transducer surfaces, responsive to the pH associated with the transducers (see FIG. 16).

In one aspect, transducers 102a and 102b both have bonds to a first functional molecule, and the fluid multiplexer 812 introduces a second functional molecule to the fluid chamber environment 808. The voltage demultiplexer 816 creates a difference between the pH associated with the transducers 102a and 102b, and selectively binds the second functional molecules to the first functional molecules of transducer 102a (see FIG. 10), but not to the first functional molecules of transducer 102b.

In a different aspect, transducers 102a and 102b both have bonds to a second molecule, and the fluid multiplexer 812 introduces a third molecule to the fluidic chamber 808. The voltage demultiplexer 816 creates a difference between the pH associated with transducers 102a and 102b, selectively activating the second molecule with the third molecule to form a first functional molecule bound to the first transducer (see FIG. 7). In this aspect, the first functional molecule is not formed on transducer 102b.

In one aspect, transducers 102a and 102b both have bonds to a second molecule, and the fluid multiplexer 812 introduces a first functional molecule to the fluidic chamber 808. The voltage demultiplexer 816 creates a difference between the pH associated with the transducer's 102a and 102b to selectively modify the second molecule bond to transducer 102a, and bind the first functional molecule to the modified second functional molecule. In this aspect, the second molecule attached to transducer 102b is not modified (see FIG. 6).

In another aspect, transducers 102a and 102b both have a bond to a second molecule, and the fluid multiplexer 812 introduces a third molecule to the fluidic chamber 808. The voltage demultiplexer 816 creates a difference between the pH associated with transducers 102a and 102b, selectively activating the third molecule, and joining the activated third molecule with the second molecule to form a first functional molecule bound to the first transducer.

Electrochemical Manipulation of pH for Immobilization Control

Returning to FIGS. 9A and 9B, it can be seen that the counter electrode 806 and the pH generating electrode 900 are connected with an external voltage generator 902 capable of applying voltage to the pH generation electrode. The counter electrode is used to complete the circuit. In some cases, the transducer can itself be used as a pH generating electrode (FIG. 9B), providing that its surface is conductive, and that this conductive application does not interfere with the biochemical transducer functioning. When a cathodic voltage is applied to the pH generating electrode 900, the pH of the surrounding medium is increasing due to the reaction 1:

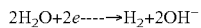
$$2H_2O + 2e^- \longrightarrow H_2 + 2OH^-$$ reaction 1,

Anodic voltage results in proton generation due to the reaction 2:

$$2H_2O - 4e^- \longrightarrow 4H^+ + O_2$$ reaction 2

FIG. 10 presents an example of the pH-controlled immobilization of a bio-component 200a initially bound with, or functionalized with a group Z. Transducers 102a and 102b, shown as surrounding and in close proximity to pH-generating electrodes 900a and 900b, respectively (also see the plan view of pH-generating electrode 900 in FIG. 9A), of an array 802 are functionalized with a group X (see FIG. 2). The pH-controlled immobilization promotes the specific attachment of a bio-component 200a to transducer 102a, while maintaining transducer 102b intact. To achieve this goal, a pH value favorable for immobilization is generated in a close proximity of transducer 102a. The vicinity of transducer 102b maintains a pH value unfavorable for immobilization. The bio-component 200a is then introduced to the reaction medium, and it is exclusively immobilized at transducer 102a.

Figure 11:
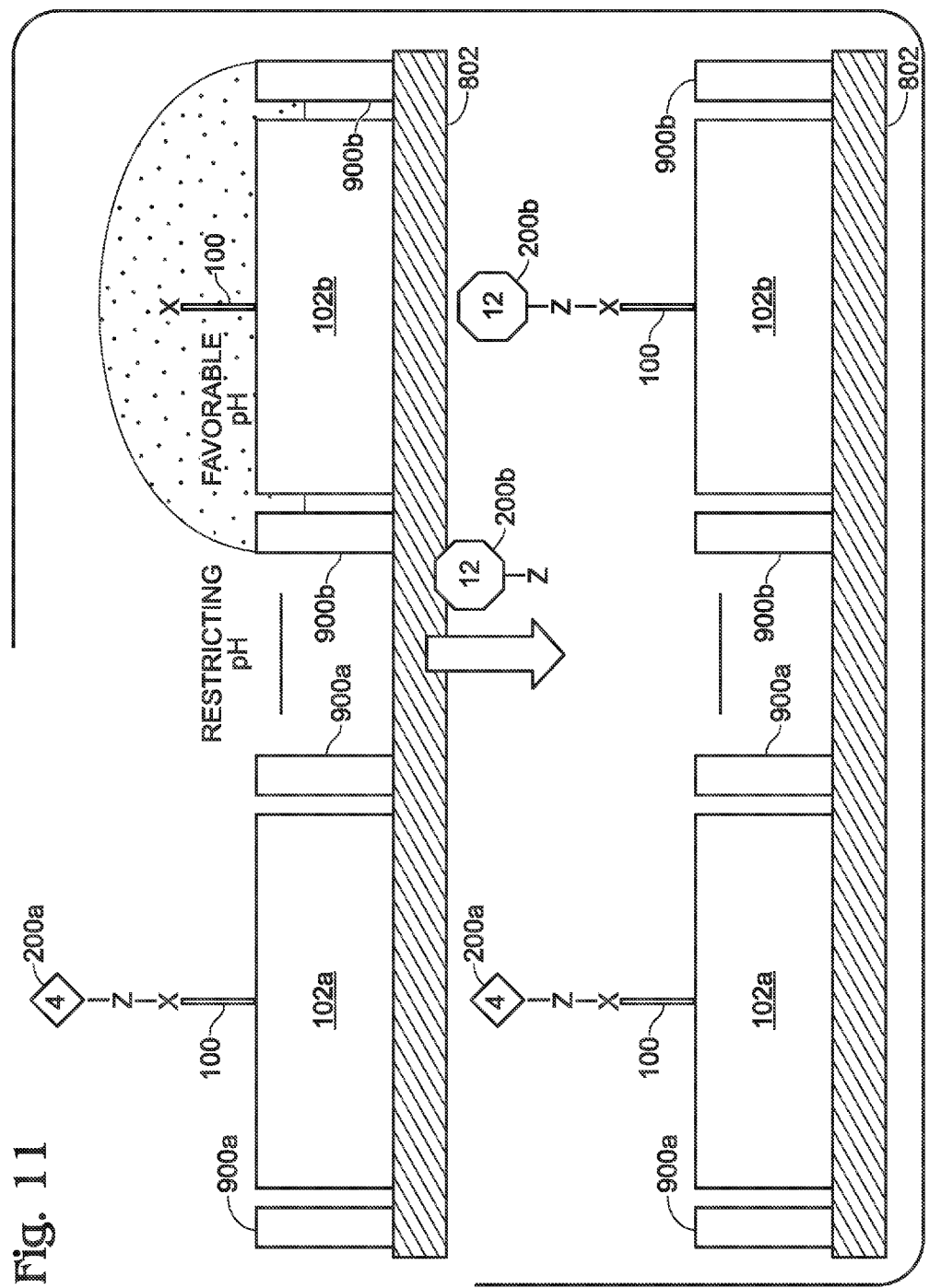
FIG. 11 continues the example started in FIG. 10.

FIG. 11 continues the example started in FIG. 10. Next, a different bio-component 200b, modified with the group Z, is immobilized in a similar, pH-controlled manner on the surface of transducer 102b. As the result, two different bio-components 200a and 200b, both modified with the same group Z, are sequentially attached to different transducers in a desired array configuration.

Figure 12:
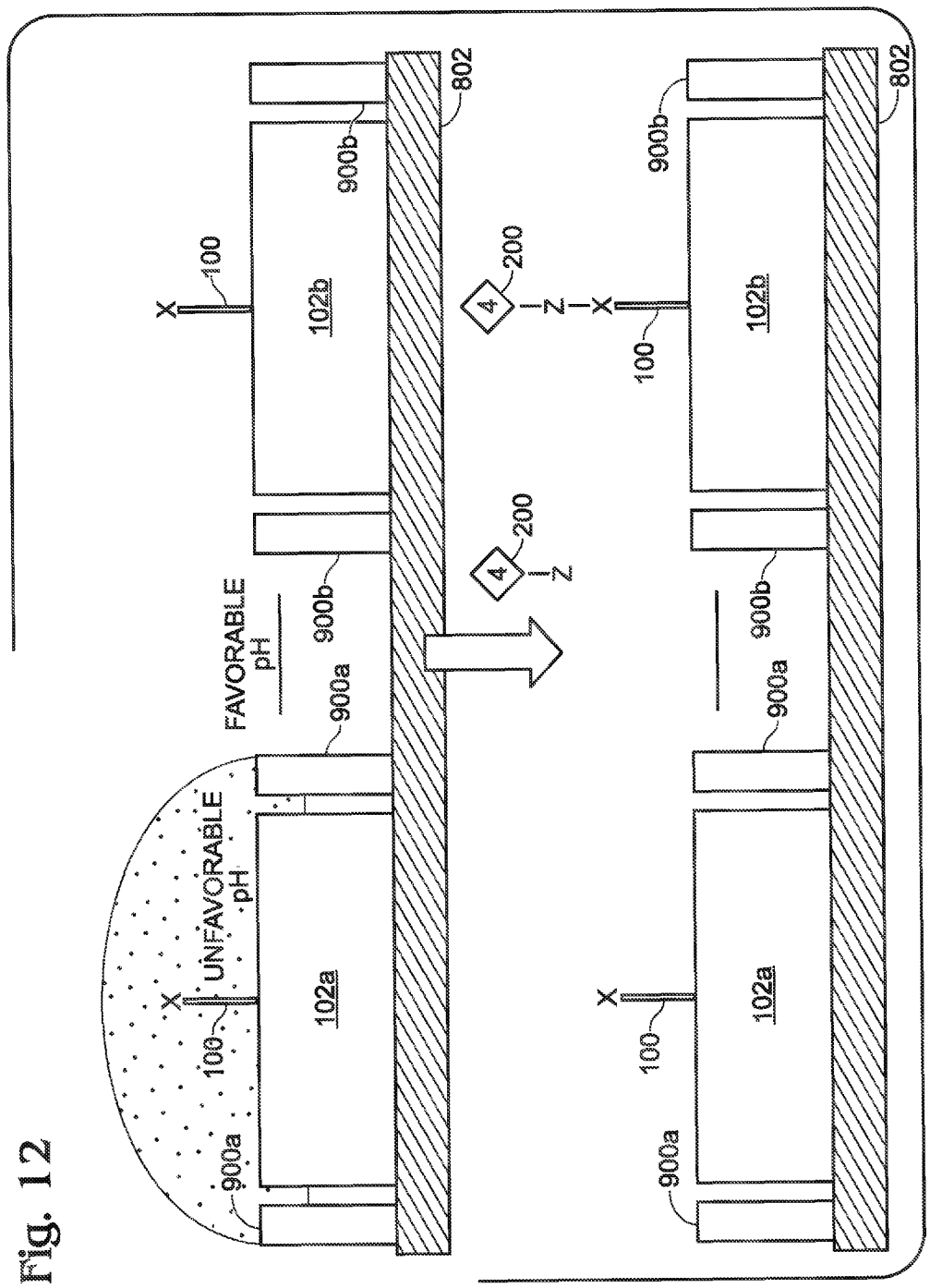
FIG. 12 demonstrates a pH-controlled immobilization alternative to the method presented in FIG. 10.

FIG. 12 demonstrates a pH-controlled immobilization alternative to the method presented in FIG. 10. In this case, the restricting pH is generated at transducer 102a, where immobilization of the bio-component 200 is undesired. The immobilization of bio-component 200 occurs exclusively at the desired transducer 102b. Sequential steps of pH-controlled immobilization lead to creation of a transducer array of any desired configuration.

Figure 13:
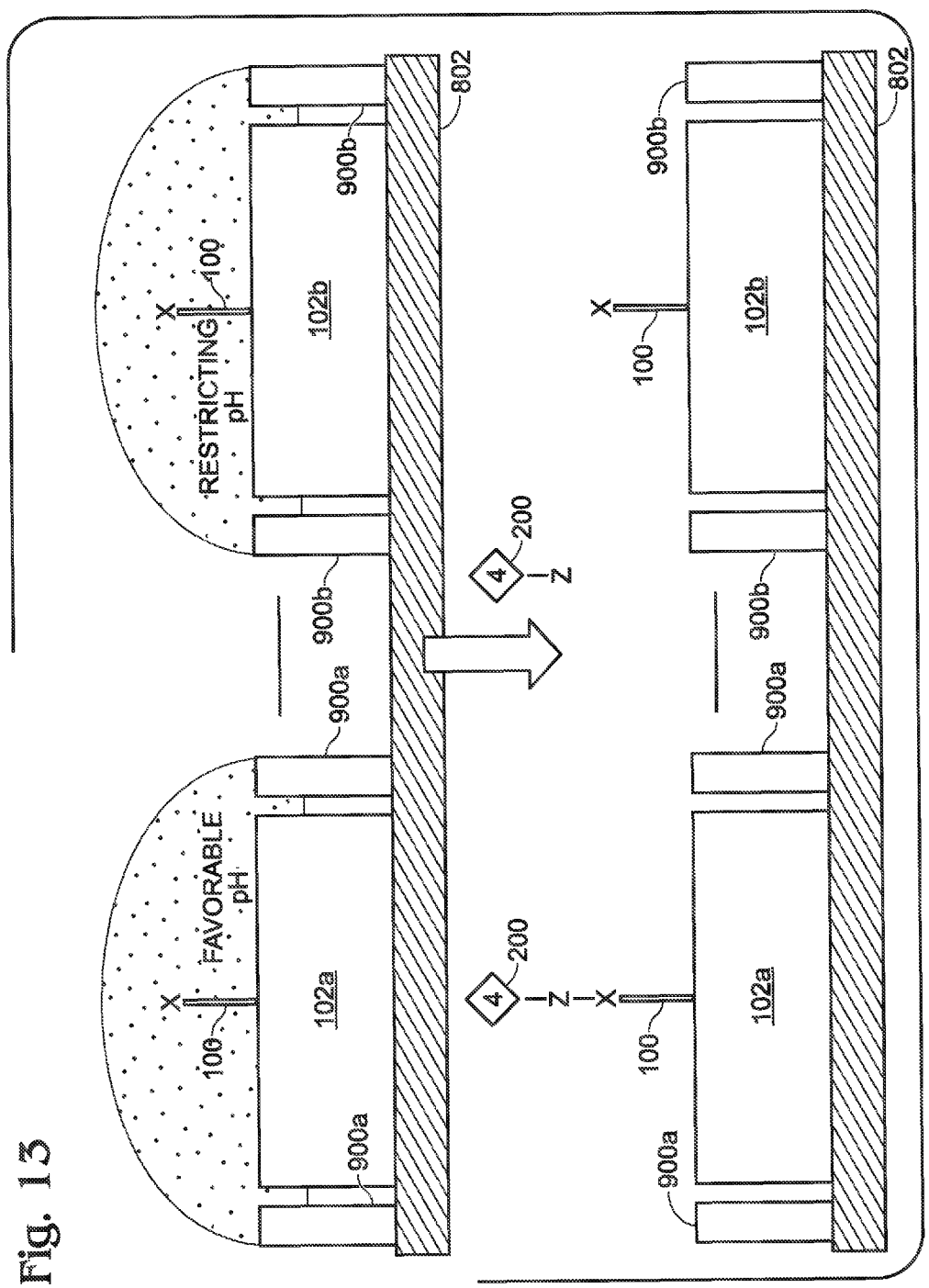
FIG. 13 presents an example of pH-controlled immobilization where both favorable and restricting pH conditions are created simultaneously by electrochemical pH generation.

FIG. 13 presents an example of pH-controlled immobilization where both favorable and restricting pH conditions are created simultaneously by electrochemical pH generation. The reaction medium can simultaneously support any number of different pH values, since the pH value in the vicinity of one transducer 102a/102b, shown as surrounding and in close proximity to a respective pH-generating electrode 900a/900b, does not affect the immobilization conditions in an adjacent transducer surface vicinity.

Figure 14:
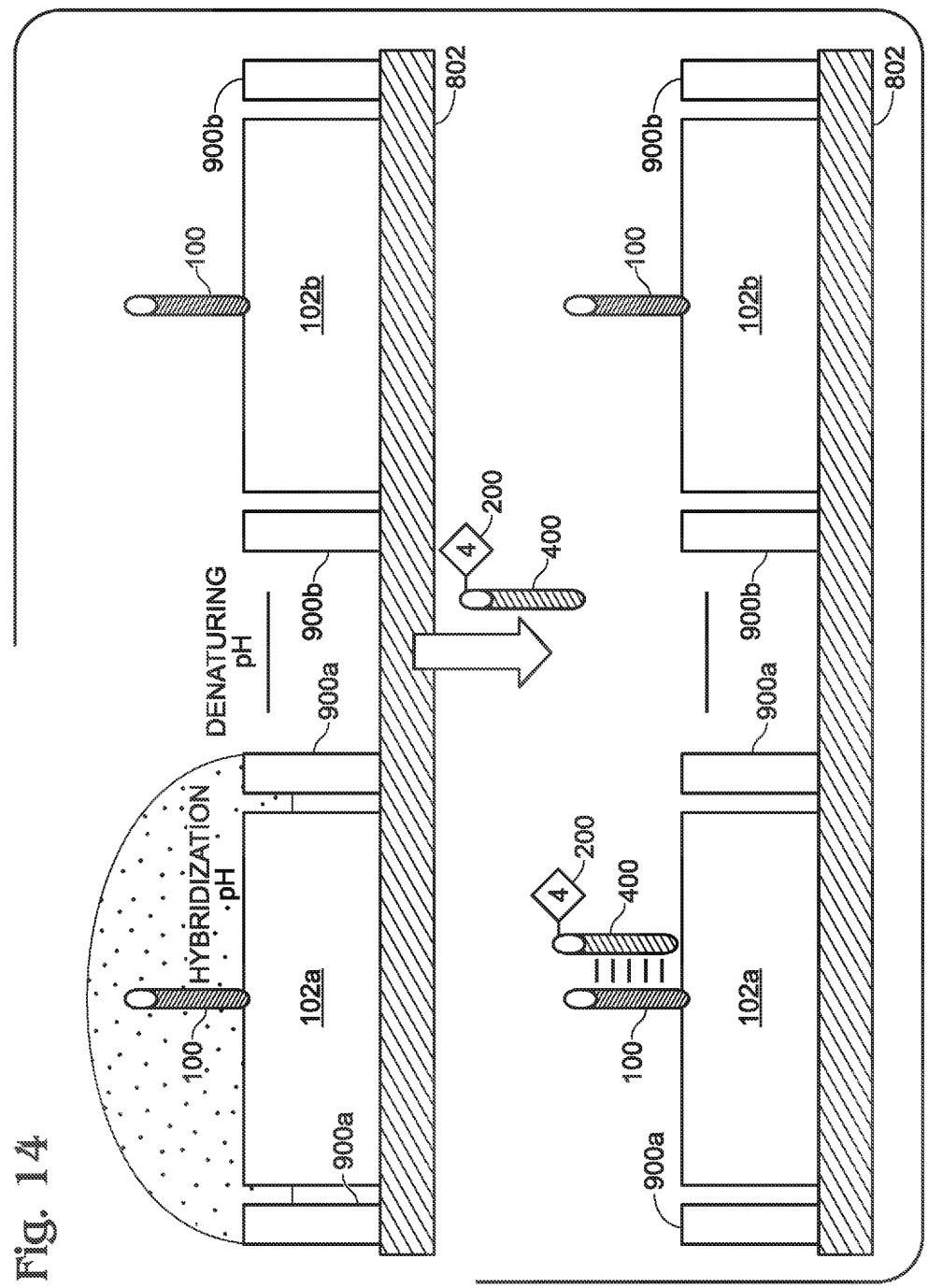
FIG. 14 shows an example of pH-controlled immobilization of a bio-component modified with a specific oligonucleotide tag.

FIG. 14 shows an example of pH-controlled immobilization of a bio-component 200 modified with a specific oligonucleotide tag 400. The surface of transducers and 102b, and 102b, shown as surrounding and in close proximity to pH-generating electrodes 900a and 900b, respectively, are modified with an oligonucleotide 100. The tag 400 is designed to be complementary to the surface oligonucleotide 100. Hybridization of the surface oligonucleotide with the tag 400 of the bio-component 200 leads to attachment of the latter onto the transducer surface via oligonucleotide 100. This process occurs only at pH conditions favorable for oligonucleotides hybridization (close to neutral pH value). The reaction medium has a pH value that prevents double stranded structure formation (denaturing pH). A pH value favorable for hybridization is generated electrochemically at the vicinity of the transducer 102a surface. As the result, immobilization of the bio-component 200 occurs exclusively on the surface of the selected transducer 102a. The reaction medium with another bio-component modified with oligonucleotide tag 100 can then be introduced to the array. A next cycle of the pH-controlled immobilization, can then be performed to attach another bio-component to a desired set of the transducers on the array.

Figure 15:
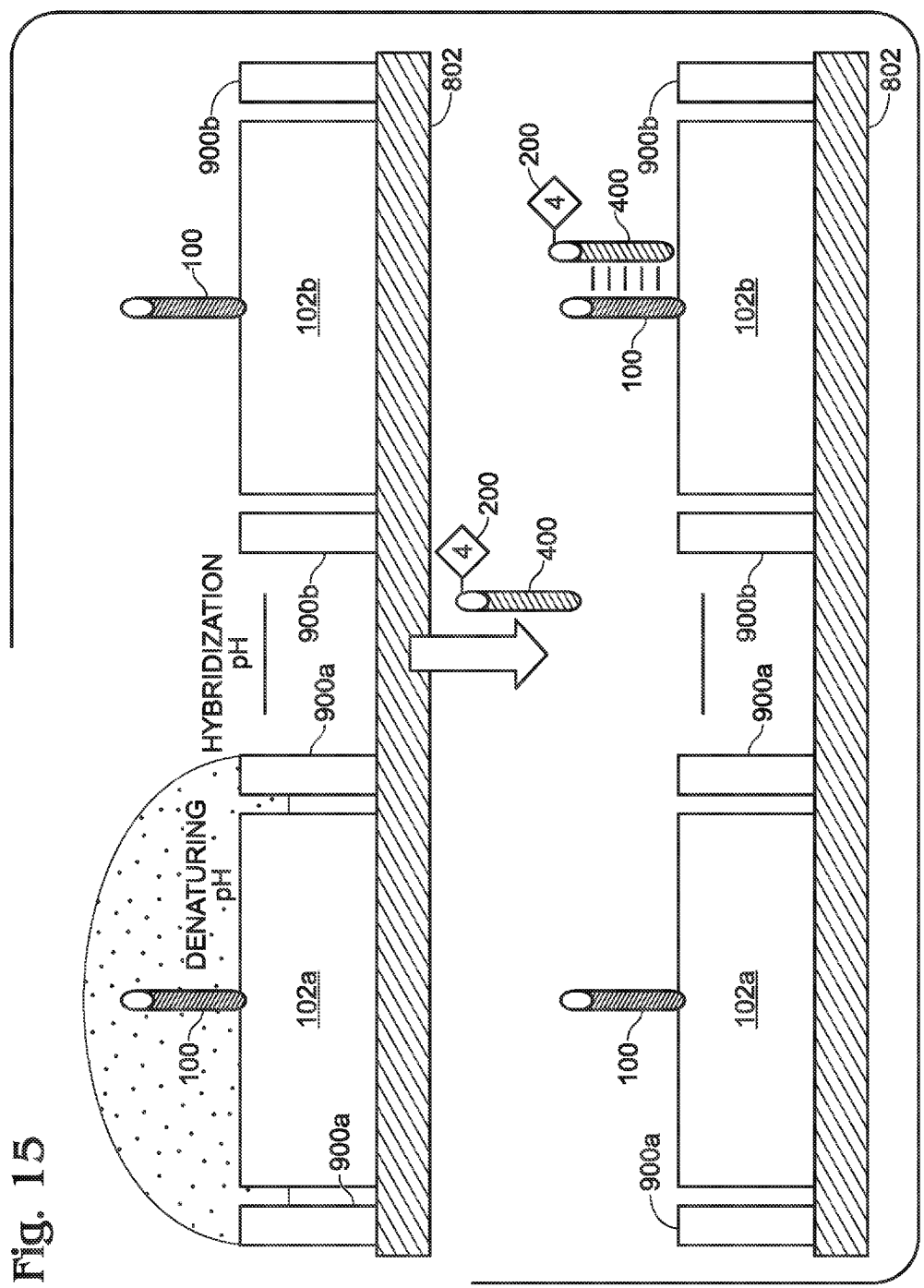
FIG. 15 depicts a variation of the pH-controlled immobilization of a bio-component modified with a specific oligonucleotide tag.

FIG. 15 depicts a variation, of the pH-controlled immobilization of a bio-component modified with a specific oligonucleotide tag. In contrast to FIG. 14, in this case the denaturing pH is generated at transducers 102a, shown as surrounding and in close proximity to pH-generating electrode 900a, where immobilization of the bio-component 200 is undesired. The immobilization of bio-component 200 occurs exclusively at the desired transducer 102b, which surrounds and is in close proximity to pH-generating electrode 900b.

Figure 16:
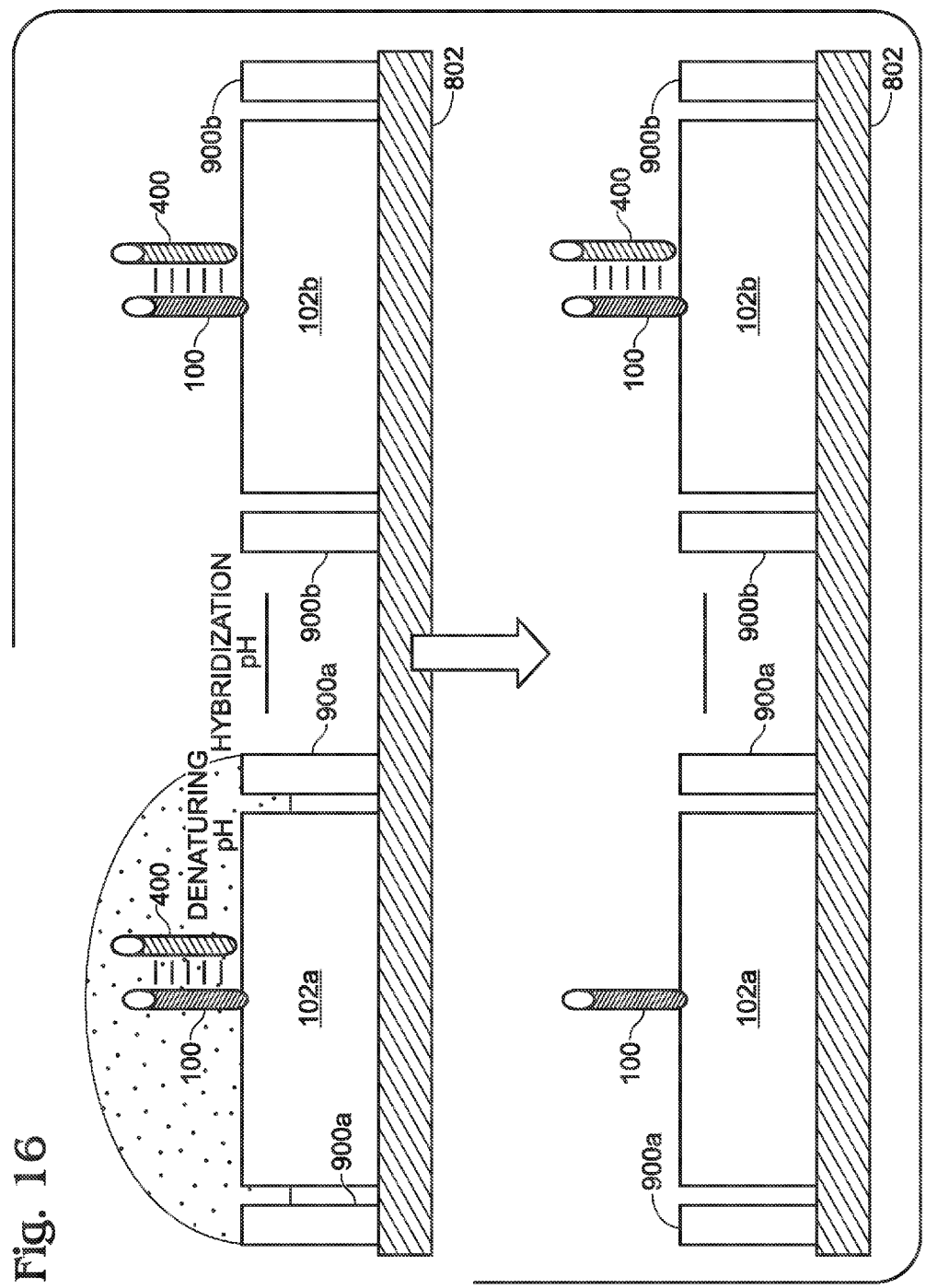
FIG. 16 demonstrates the pH-controlled immobilization of the bio-component modified with a specific oligonucleotide tag, already formed on transducer surface.

FIG. 16 demonstrates the pH-controlled immobilization of the oligonucleotide 100 modified with a specific oligonucleotide tag 400, already formed on transducer surface 102a, shown as surrounding and in close proximity to pH-generating electrode 900a. Likewise, transducer surface 102b is shown surrounding and in close proximity to pH-generating electrode 900b. The reversible nature of oligonucleotide hybridization permits pH-controlled immobilization of oligonucleotide tagged bio-components through controlled denaturing of pre-blocked transducer surface. In FIG. 16 the whole field of transducers is pre-hybridized with oligonucleotides 400. These oligonucleotides serve to block the transducers from binding with any other oligonucleotide tagged functional molecules (such as molecule 200 depicted in FIG. 15).

Figure 17:
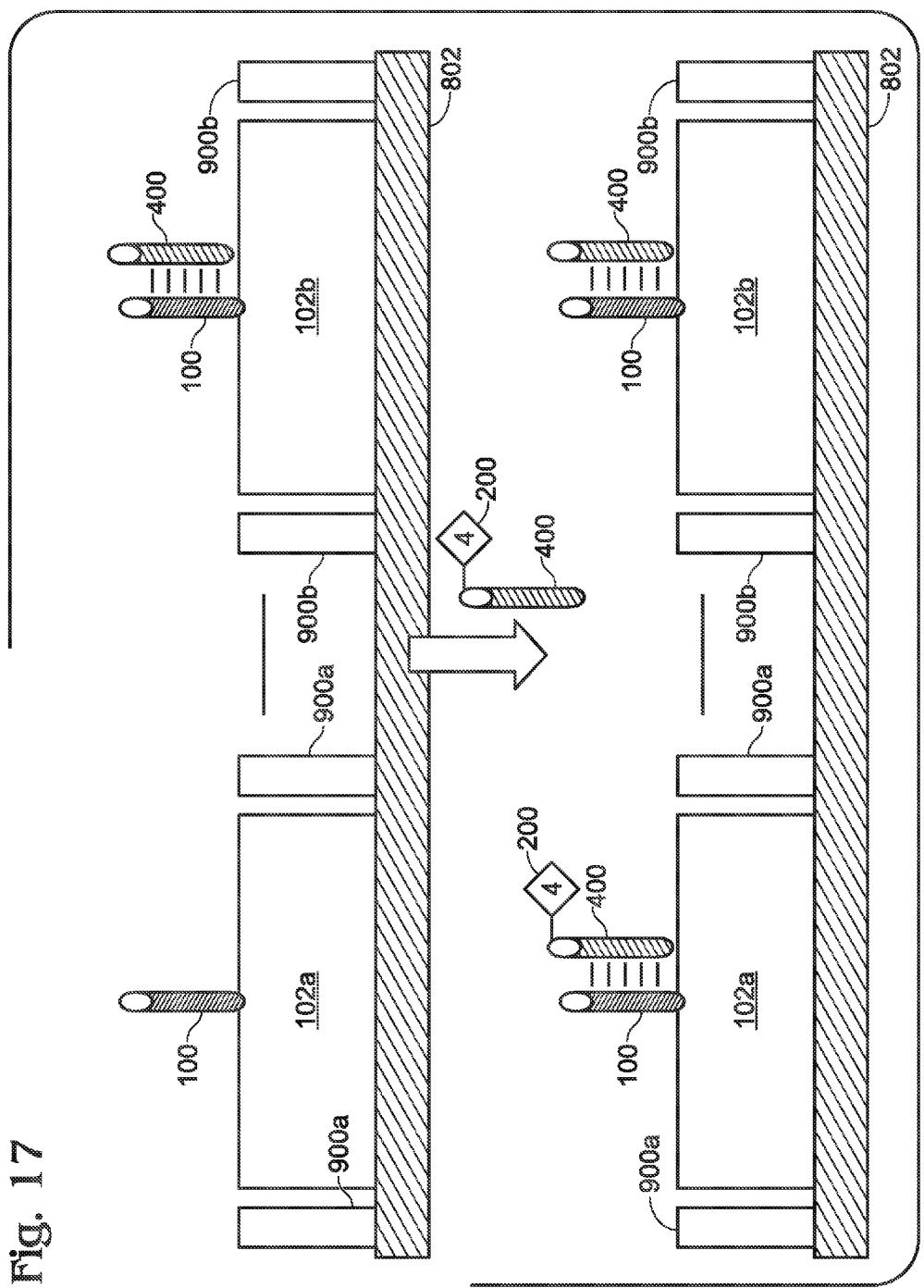
FIG. 17 depicts the continuation of the process started in FIG. 16.

FIG. 17 depicts the continuation of the process started in FIG. 16. In FIG. 16, the surface of transducers 102a and 102b are bonded to oligonucleotide 100, and initially incubated with the oligonucleotide 400, which has the same structure as the oligonucleotide tag of the bio-component of FIG. 15. The incubation results in formation of double stranded complexes of oligonucleotides 100 and 400 on transducer 102b. In FIG. 17, the generation of a high pH at a transducer 102a results in a denaturing of the DNA double stranded bound and 'knocks off' the blocking molecule. After that, transducer 102a is deblocked and becomes capable of binding to an oligonucleotide tagged molecule (such as molecule 200 depicted in FIG. 15).

FIG. 18 is a flowchart illustrating a method for selectively functionalizing a transducer microarray. Although the method is depicted as a sequence of numbered steps for clarity, the numbering does not necessarily dictate the order of the steps. It should be understood that some of these steps may be skipped, performed in parallel, or performed without the requirement of maintaining a strict order of sequence. The method starts at Step 1800.

Step 1802 provides a microarray including a field of transducers exposed to a shared local environment. Typically, each transducer is associated with an adjacent pH-generating electrode. Step 1804 creates a difference in pH associated with the transducers. Step 1806 selectively binds first functional molecules to transducers in response to the pH associated with the transducers. Some examples of functional molecules include oligonucleotides, DNA, RNA, DNA fragments, RNA fragments, peptides, receptors, antibodies, enzymes, whole cells, cellular fragments, biotin, and streptavidin.

In one aspect, providing the micro-array in Step 1802 includes providing a pH-generating electrode associated with each transducer, and a counter electrode. Then, creating the difference in pH associated with the transducers in Step 1804 includes substeps. Step 1804 selectively applies a voltage potential between pH-generating electrodes and the counter electrode, and creates a difference of pH in regions adjacent to the transducers.

In one aspect, Step 1803a introduces the first functional molecules to the environment. Then, creating the difference in pH associated with the transducers in Step 1804 includes modifying the pH associated with a first transducer, while maintaining the pH associated with a second transducer. Step 1806 binds the first functional molecules from the environment to the first transducer, but not the second transducer. Alternately, selectively binding the first functional molecules to transducers in Step 1806 includes binding the first functional molecules from the environment to the second transducer, but not the first transducer.

In a different aspect, selectively binding the first functional molecules to transducers in Step 1806 includes disassociating a bond between first functional molecules and transducer surfaces, responsive to the pH associated with the transducers.

In one aspect, selectively binding the first functional molecules to transducers in Step 1806 includes selectively binding first functional molecules to a first transducer and a second transducer. Then, Step 1808 introduces a second functional molecule to the environment. Step 1810 creates a second difference between the pH associated with the first and second transducers. Step 1812 selectively binds the second functional molecules to the first functional molecules on the first transducer, in response to the pH associated with the first transducer. In this aspect, the second functional molecule is not bound to the first functional molecule on the second transducer.

In another aspect, Step 1802 provides first and second transducers having an attached second molecule. Step 1803b introduces a third molecule to the environment. Step 1804 creates a difference between the pH associated with the first and second transducers, and Step 1806 activates the second molecule with the third molecule to selectively form the first functional molecule bound to the first transducer (but not the second transducer).

In another aspect, Step 1802 provides first and second transducers both having a bond to a second molecule, and Step 1803*a* introduces the first functional molecule to the environment. Step 1804 creates a difference between the pH associated with the first and second transducers, and Step 1806 selectively modifies the second molecule, and joins the first functional molecule with the modified second functional molecule. Depending upon which transducer generates the pH, and whether the pH is favorable to the reaction, the modified second functional molecule may be bound to either the first or second transducer.

In a different aspect, Step 1802 provides first and second transducers both having a bond to a second molecule, and Step 1803*b* introduces a third molecule to the environment. Step 1804 creates a difference between the pH associated with the first and second transducers, and Step 1806 selectively activates the third molecule, and joins the activated third molecule to the second molecule to form the first functional molecule attached to the first transducer.

A system and method for functionalizing a transducer microarray have been presented. Examples of specific procedures and materials have been used to illustrate the invention. However, the invention is not necessarily limited to just these examples. Other variations and embodiments of the invention will occur to those skilled in the art.

I claim:

1. A method for selectively functionalizing a transducer microarray, the method comprising:
   providing a microarray including a field of transducers exposed to a shared local environment, a pH-generating electrode associated with each transducer, and a counter electrode;
   creating a first difference in pH associated with the transducers as follows:
      selectively applying a voltage potential between pH-generating electrodes and the counter electrode;
      creating a difference of pH in the environment overlying the transducers; and,
   selectively binding first functional molecules to transducers in response to the pH associated with the transducers.

2. The method of claim 1 further comprising:
   introducing the first functional molecules to the environment;
   wherein creating the first difference in pH associated with the transducers includes modifying the pH associated with a first transducer, while maintaining the pH associated with a second transducer; and,
   wherein selectively binding the first functional molecules to transducers includes binding the first functional molecules from the environment to the first transducer, but not the second transducer.

3. The method of claim 1 wherein selectively binding the first functional molecules to transducers includes selectively binding a first functional molecule selected from a group consisting of: oligonucleotides, DNA, RNA, DNA fragments, RNA fragments, peptides, receptors, antibodies, enzymes, whole cells, cellular fragments, biotin, and streptavidin.

4. The method of claim 1 wherein providing the microarray includes providing a field of transducers, where each transducer is associated with a pH-generating electrode.

5. A system for selectively functionalizing a transducer microarray, the system comprising:
   a microarray including a field of transducers, with a pH-generating electrode associated with each transducer, and a counter electrode;
   a fluidic chamber including a cavity to provide a shared local environment for the field of transducers;
   a fluid demultiplexer to selectively supply fluids to the fluidic chamber; and,
   a voltage demultiplexer connected to the microarray to create a voltage potential between the counter electrode and the pH-generating electrodes of selected transducers, wherein a difference is created in the pH associated with transducers, responsive to the pH in the fluids overlying the transducers, for selectively binding functional molecules to transducers.

6. The system of claim 5 wherein the fluid multiplexer introduces a first functional molecule to the fluidic chamber; and,
   wherein the voltage demultiplexer modifies the pH associated with a first transducer, while maintaining the pH associated with a second transducer, thereby binding the first functional molecules in the fluidic chamber to the first transducer, but not the second transducer.

7. The system of claim 5 wherein the transducers are bound to functional molecules selected from a group consisting of: oligonucleotides, DNA, RNA, DNA fragments, RNA fragments, peptides, receptors, antibodies, enzymes, whole cells, cellular fragments, biotin, and streptavidin.

* * * * *